United States Patent
Jugert et al.

(10) Patent No.: US 11,366,053 B2
(45) Date of Patent: Jun. 21, 2022

(54) FLOW-THROUGH MEASURING STATION

(71) Applicant: Endress+Hauser Conducta GmbH+Co. KG, Gerlingen (DE)

(72) Inventors: Stephan Jugert, Dresden (DE); Thomas Pfauch, Leipzig (DE); Holger Lippert, Leisnig (DE); Hongshuo Domnick, Dresden (DE)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 312 days.

(21) Appl. No.: 16/701,827

(22) Filed: Dec. 3, 2019

(65) Prior Publication Data
US 2020/0173974 A1 Jun. 4, 2020

(30) Foreign Application Priority Data
Dec. 4, 2018 (DE) .................. 10 2018 130 834.5

(51) Int. Cl.
*G01N 21/05* (2006.01)
*G01N 33/18* (2006.01)
*G01N 33/49* (2006.01)

(52) U.S. Cl.
CPC ...... *G01N 21/05* (2013.01); *B01L 2300/0877* (2013.01); *G01N 33/1893* (2013.01); *G01N 33/4915* (2013.01)

(58) Field of Classification Search
CPC ............. G01N 21/05; G01N 33/1893; G01N 33/4915; B01L 2300/0877
See application file for complete search history.

(56) References Cited

U.S. PATENT DOCUMENTS

| 8,615,374 | B1 | 12/2013 | Discenzo |
| 2005/0228609 | A1 | 10/2005 | Moscaritolo et al. |
| 2008/0011076 | A1* | 1/2008 | Buck ............ F16K 15/025 73/861.47 |
| 2013/0218352 | A1* | 8/2013 | Iovanni ............ G01N 30/465 700/282 |

(Continued)

FOREIGN PATENT DOCUMENTS

| CN | 102109365 A | 6/2011 |
| CN | 104677410 A | 6/2015 |

(Continued)

OTHER PUBLICATIONS

Endress+Hauser, Operating Instructions Flowfit W CCA250 Flow assembly for chlorine sensors, 20 pp.

*Primary Examiner* — Nathaniel J Kolb
(74) *Attorney, Agent, or Firm* — Christopher R. Powers; Endress+Hauser (USA) Holding Inc.

(57) ABSTRACT

A flow-through measuring station includes at least one flow cell having a fluid channel. The fluid channel has a fluid inlet and a fluid outlet and is configured to conduct a liquid medium. One or more flow cells each include at least one sensor configured to be contacted with the medium and to determine at least one respective media property. At least one illumination unit is configured to indicate a respective state of at least one sensor. The measuring station also includes a transmitter/measuring transducer which is configured to operate the at least one sensor and the at least one illumination unit, and to determine in each case a state of at least one sensor.

16 Claims, 2 Drawing Sheets

(56) References Cited

U.S. PATENT DOCUMENTS

2014/0259410 A1* 9/2014 Zerhusen ............. A61G 7/0507
  5/600
2016/0012705 A1* 1/2016 Baret ..................... G08B 21/18
  340/603
2018/0117590 A1* 5/2018 Andreyev ......... B01L 3/502715

FOREIGN PATENT DOCUMENTS

| CN | 205002797 U | 1/2016 |
|---|---|---|
| CN | 206929116 U | 1/2018 |
| CN | 207351949 U | 5/2018 |
| CN | 108444535 A | 8/2018 |
| CN | 108474685 A | 8/2018 |
| CN | 108519472 A | 9/2018 |
| DE | 102013107964 A1 | 1/2015 |
| EP | 2233994 A2 | 9/2010 |

* cited by examiner

FLOW-THROUGH MEASURING STATION

CROSS-REFERENCE TO RELATED APPLICATION

The present application is related to and claims the priority benefit of German Patent Application No. 10 2018 130 834.5, filed on Dec. 4, 2018, the entire contents of which are incorporated herein by reference.

TECHNICAL FIELD

The present disclosure relates to a flow-through measuring cell having at least one flow cell in which there is at least one sensor for detecting a media property of a medium flowing through the flow cell.

BACKGROUND

For example, the FlowFit CCA 250 measuring cell from Endress+Hauser is such a measuring cell which is suitable for accommodating a plurality of sensors.

The FlowFit CCA 250 measuring cell is capable of detecting states of sensors and outputting these states by means of a transmitter/measuring transducer. It has been shown that it is cumbersome and complicated for technicians to be able to determine the state of sensors via just the transmitter/measuring transducer. This is undesirable, for example, in prescribed or routine maintenance rounds.

SUMMARY

The object of the present disclosure is to propose a flow-through measuring station in which a plant operator receives information about states of sensors more quickly.

The object is achieved via a flow-through measuring station according to the present disclosure.

A flow-through measuring station according to the present disclosure comprises at least one flow cell having a respective fluid channel, wherein the fluid channel has a fluid inlet and a fluid outlet, and wherein the fluid channel is configured to conduct a liquid medium. At least one sensor is arranged in or on a flow cell, wherein each flow cell has at least one sensor, wherein the at least one sensor is configured to be contacted with the medium and to determine at least one respective media property. At least one illumination unit is mechanically connected to the flow measuring cell.

The measuring station comprises a transmitter/measuring transducer which is configured to operate the at least one sensor and the at least one illumination unit and to determine in each case a state of at least one sensor, wherein the at least one illumination unit is configured separately from the sensor and transmitter/measuring transducer, and wherein the at least one illumination unit is configured to indicate a respective state of at least one sensor. For example, the sensor is configured to determine the concentration of at least one substance in the medium or a pH value.

The term "state" refers in this case to a functionality or operating state of the sensor. For example, exceeding a limit value of a measured value of a measurement signal may cause an optical signal to be triggered by means of the illumination unit.

Depending on the state of the at least one monitored sensor, an optical signal can be output in the area of the flow measuring cell by means of the illumination unit. For example, the signals can be encoded according to the Namur 107 standard dated 10 Apr. 2017. This would identify a sensor failure with red, a function check of the sensor with orange, a sensor operation outside of a specification with yellow, a maintenance requirement of the at least one sensor with blue, and a diagnosis with green.

In one embodiment, the measuring station has at least two sensors which are arranged in or on at least one flow cell, and wherein the at least one illumination unit is configured to display the states of at least two sensors in a sensor-specific manner.

In one embodiment, the measuring station has at least two flow cells and an illumination unit for each flow cell.

In one embodiment, at least one flow measuring cell has at least two sensors, and wherein an illumination unit is associated with at least one flow measuring cell having at least two sensors, and wherein the illumination unit is configured to indicate a respective state of individual sensors of the associated flow measuring cell.

In one embodiment, the illumination unit comprises at least one respective signal lamp for individual sensors or individual flow cells.

In one embodiment, one or more signal lamps belonging to a sensor or to a flow cell are configured to emit light of different colors. Further, a signal lamp belonging to a sensor or a flow cell is configured to emit light having a selectable color.

In one embodiment, the transmitter/measuring transducer is connected to the signal lamps by means of connecting electrical cables, or wherein the illumination unit or the signal lamp has a microcontroller, which microcontroller is configured to activate the signal lamps, wherein the transmitter/measuring transducer is connected to the microcontroller by means of a connecting electrical cable. Or, the illumination unit has an LED strip which can be activated by means of a connecting electrical cable, wherein the LED strip has a plurality of LEDs or LED groups which are respectively associated with a sensor or a flow cell.

In one embodiment, the illumination unit can be instructed by means of the transmitter/measuring transducer to operate at least one signal lamp in a flashing or pulsating manner. The flashing or pulsing may also be a luminous intensity variation without completely switching off the illumination unit.

In one embodiment, the measuring station has at least one command interface by means of which command interface external commands can be received, wherein the transmitter/measuring transmitter is configured to cause the illumination unit to operate at least one signal lamp in a flashing manner if a corresponding command is input.

In one embodiment, the flow cell is of modular design, wherein modules of the flow cell are configured to respectively accommodate at least one sensor. In one embodiment, at least one signal lamp is associated with each module.

In one embodiment, the signal lamp respectively has at least one illuminant from the following list: LED, OLED, multicolor LED. According to one example, the illuminants are arranged on a light strip.

In one embodiment, state signals correspond to the Namur standard Namur 107 dated 10 Apr. 2017.

In one embodiment, the flow cell has a flow/media indicator, wherein the flow/media indicator, in some embodiments, includes an inductive proximity switch, and at least one illumination unit is configured to indicate a respective state of the flow/media indicator.

In one embodiment, the flow indicator is arranged in a module.

In one embodiment, the flow/media indicator is configured to output a warning message in the case of a low flow rate.

BRIEF DESCRIPTION OF THE DRAWINGS

The present disclosure will be described in the following with reference to exemplary embodiments.

DETAILED DESCRIPTION

Figure 1:
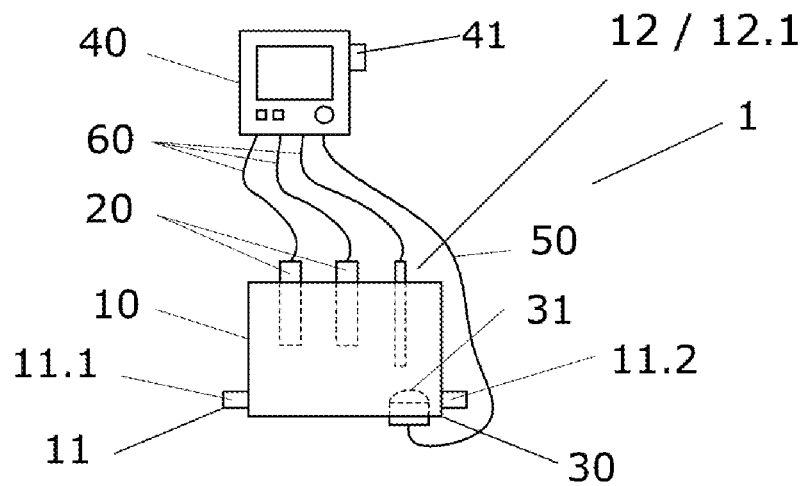
FIG. 1 shows a schematic design of an exemplary embodiment of the present disclosure.

FIG. 1 shows a flow-through measuring station 1 with a flow cell 10, sensors 20 to record respectively at least one media property of a medium located in the flow cell, an illumination unit 30 for outputting a state of at least one sensor by means of a signal lamp 31, a transmitter/measuring transducer 40 for operating the sensors and the illumination unit, a connecting electrical cable 50 for connecting the illumination unit to the transmitter/measuring transmitter, and electrical sensor connector cables 60 for connecting the sensors to the transmitter/measuring transducer. In this case, the sensors 20 are arranged in the flow cell and are in contact with the medium. The flow cell has a fluid channel 11 with a fluid inlet 11.1 and a fluid outlet 11.2, wherein the fluid channel is configured to guide the medium past the sensors. As shown here, the transmitter/measuring transducer may have a command interface 41 by means of which command interface commands can be received, for example from a remote control center.

Alternatively, the sensors may be arranged on the flow measuring cell without media contact and may be based on a contactless measuring principle. A measuring station according to the present disclosure may also comprise only one sensor.

The transmitter/measuring transducer is configured to monitor at least one sensor. Depending on the state of the at least one monitored sensor, an optical signal may be output in the area of the flow measuring cell by means of the illumination unit. For example, the signals may be encoded in accordance with the Namur 107 standard dated 10 Apr. 2017. This would identify a sensor failure with red, a function check of the sensor with orange, a sensor operation outside of a specification with yellow, a maintenance requirement of the at least one sensor with blue, and a diagnosis with green. As an alternative to the variant shown in FIG. 1, a respective signal lamp 31 can also be set up for a plurality of sensors 20, and a state of the individual sensors can be displayed. This may be used in the case of flow cells with numerous sensors, since during maintenance a technician may recognize which sensor requires attention upon viewing the flow cell.

Figure 2:
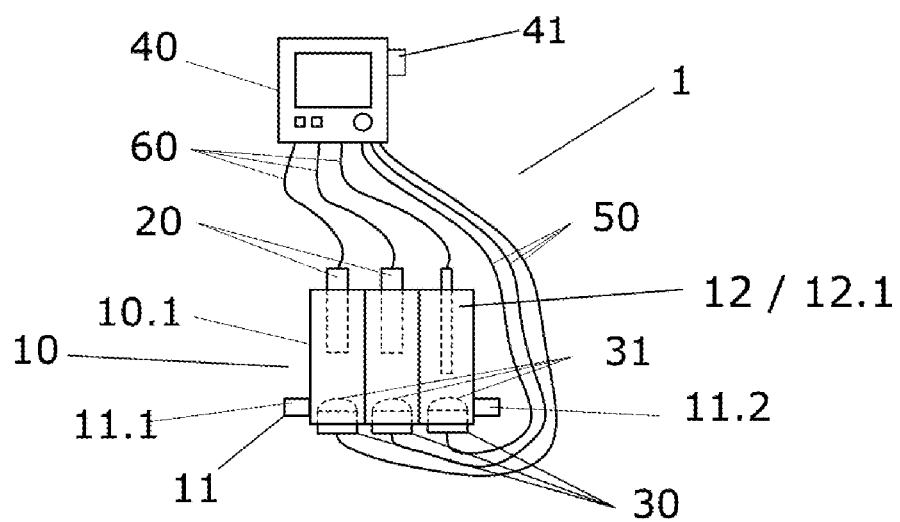
FIG. 2 shows a schematic design of an exemplary embodiment of the present disclosure.
Figure 3:
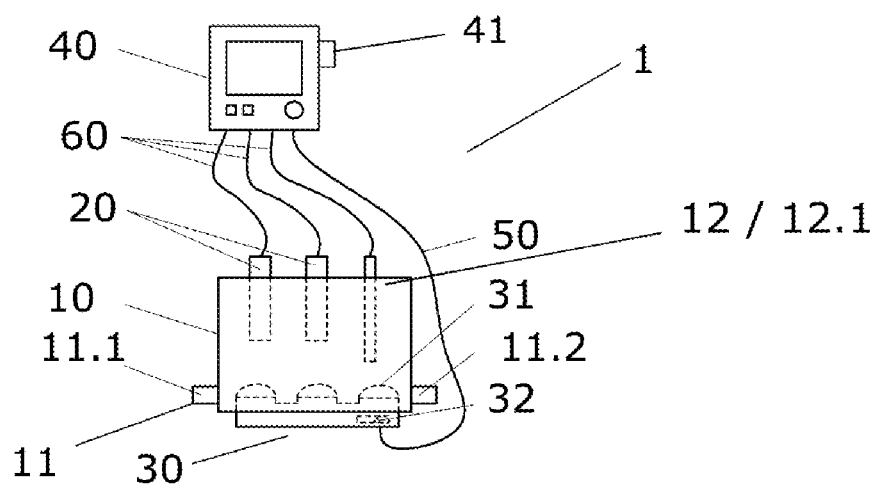
FIG. 3 shows a schematic design of an exemplary embodiment of the present disclosure.

FIG. 2 shows a further embodiment of the present disclosure in which, in contrast to the variant 10 shown in FIG. 1 and FIG. 3, the flow cell is of modular design and has modules 10.1. A sensor 20 and a signal lamp 31 are in this case associated with each module. Alternatively, a plurality of sensors may also be associated with each module.

Given flow cells with numerous sensors, a signal lamp 31 may be associated with each module, since during maintenance a technician may recognize, when viewing the flow cell, sensors of which module or which sensor requires attention.

Alternatively, only one signal lamp 31 may also be associated with the flow cell; in this way, a cost-effective measuring station can be designed.

An advantage of a modular embodiment of the flow cell is expandability in the event of a need for further sensors for liquid analysis.

FIG. 3 shows a further embodiment of the present disclosure, wherein the illumination unit has a plurality of signal lamps 31 associated with different sensors and, in contrast to the embodiments shown in FIG. 1 and FIG. 2, a microcontroller 32 for activating the signal lamps. In this instance, the transmitter/measuring transducer 40 is connected to the microcontroller 32 by means of a connecting electrical cable 60. As shown here, the flow cell 10 may be monolithic according to the embodiment shown in FIG. 1 or, alternatively may be of modular design in accordance with the embodiment shown in FIG. 2. In this instance, connecting electrical cables 60 can be saved, and the microcontroller 32 can be left to control the signal lamps 31.

A signal lamp has in each case at least one illuminant from the following list: LED, OLED, multicolor LED. The illuminant can be arranged on an LED strip, for example.

Figure 4:
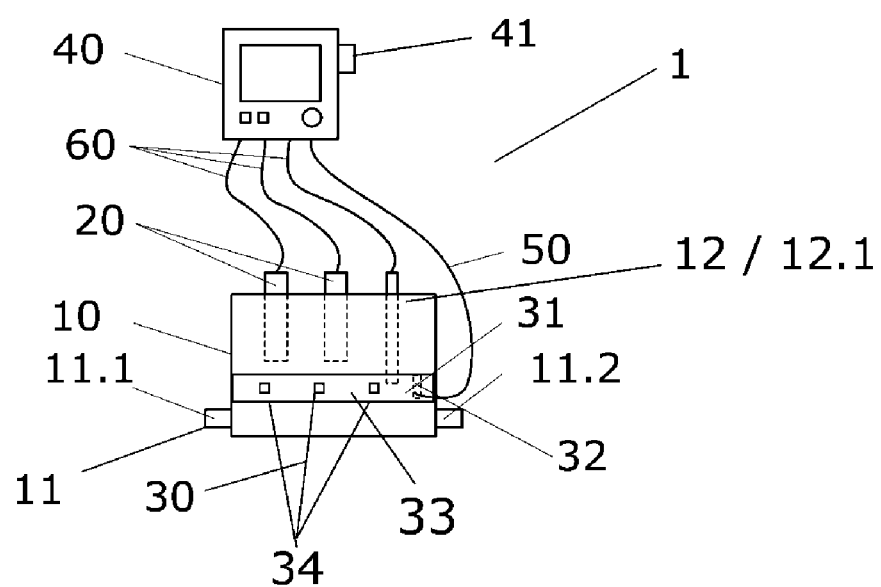
FIG. 4 shows a schematic design of an exemplary embodiment of the present disclosure.

FIG. 4 shows a further embodiment of the present disclosure in which a flow cell 10 has a plurality of sensors 20. In order to reduce a wiring outlay, contrary to the solutions proposed in FIGS. 1 to 3, a single LED strip 33 as a signal lamp 31 or a single module as a signal lamp 31 with correspondingly placed LEDs (individual lamps) extends along all the sensors 20. An LED strip with digitally activatable illuminants 34 such as RGB LEDs, or individual lamps in combination with a microcontroller 32, may be used in this case. This enables each LED or each illuminant to be activated individually. In this way, a cost-effective, sensor-specific status display can be realized. In this instance as well, the flow cell can be of modular design in accordance with FIG. 2.

As an alternative to the exemplary embodiments shown in FIGS. 1 to 4, a measuring station may also have a plurality of flow cells 10 with sensors and illumination units which are activated by means of a transmitter/measuring transducer 40.

The signal lamps 31 shown in FIGS. 1 to 4 may each be operated in a flashing manner. The transmitter/measuring transducer may activate the at least one illumination unit accordingly. Given an illumination unit with a microcontroller, the microcontroller can also be induced to activate the signal lamps accordingly. In the event that the transmitter/measuring transducer has a command interface, a command by means of which flashing of at least one illuminant is initiated may be sent via a remote control station. In a complex installation with a plurality of measuring stations, this may facilitate a rapid discovery of a measuring station that is to be serviced.

As shown in FIGS. 1 to 4, a flow cell may have a flow/media indicator 12 which is configured to detect the presence of a medium in the flow cell or of a flow of the medium, and to output a warning message if the flow is low or the medium is not present. The flow/media indicator may be an inductive proximity switch, for example.

The illumination units shown in FIGS. 1 to 4 are separate in this case from the sensors and the transmitter/measuring transducer, and are mechanically connected to the flow measuring cell. This has the advantage, for example, that, given a flow measuring cell separate from the transmitter/ measuring transducer, a technician may recognize which sensor possibly requires attention upon viewing the flow measuring cell.

The invention claimed is:

1. A flow-through measuring station, comprising:
at least one flow cell having a respective fluid channel, wherein each fluid channel has a fluid inlet and a fluid outlet, and wherein each fluid channel is configured to conduct a liquid medium;
at least one sensor which is arranged in or on a flow cell, wherein each flow cell includes at least one sensor, wherein the at least one sensor is configured to be contacted with the medium and to determine at least one respective media property;
at least one illumination unit; and
a measuring transducer configured to operate the at least one sensor and the at least one illumination unit, and to determine in each case a state of at least one sensor, wherein the measuring transducer is connected in each case to the at least one sensor using an electrical sensor connection cable,
wherein the at least one illumination unit is configured separately from the sensor and measuring transducer, and is mechanically connected to the flow measuring cell, and
wherein the at least one illumination unit is configured to indicate in each case a state of at least one sensor,
wherein the illumination unit is configured to emit a red light, an orange light, a yellow light, a blue light or a green light depending on the state of the sensor to indicate a sensor failure, a function check of the sensor, a sensor operation outside of a specification, a maintenance requirement of the sensor and a diagnosis of the sensor, respectively.

2. The measuring station of claim 1, wherein the measuring station has at least two sensors which are arranged in or on at least one flow cell, and wherein the at least one illumination unit is configured to indicate the states of the at least two sensors.

3. The measuring station of claim 1, wherein the measuring station has at least two flow cells and an illumination unit for each of the at least two flow cells.

4. The measuring station of claim 1, wherein at least one flow measuring cell has at least two sensors, and wherein an illumination unit is associated with the flow measuring cell having the at least two sensors, wherein the illumination unit is configured to indicate a respective state of individual sensors of the associated flow measuring cell.

5. The measuring station of claim 4, wherein the illumination unit comprises at least one signal lamp for individual sensors or individual flow cells.

6. The measuring station of claim 5, wherein one or more signal lamps associated with a sensor or to a flow cell are configured to emit light of different colors, or wherein a signal lamp belonging to a sensor or to a flow cell is configured to emit light having a selectable color.

7. The measuring station of claim 6, wherein the measuring transducer is connected to the signal lamps by connecting electrical cables, or wherein the illumination unit or the signal lamp includes a microcontroller, which microcontroller is configured to activate the signal lamps, wherein the measuring transducer is connected to the microcontroller by a connecting electrical cable, or wherein the illumination unit has an LED strip which can be activated via a connecting electrical cable, wherein the LED strip has a plurality of LEDs or LED groups which are respectively associated with a sensor or a flow cell.

8. The measuring station of claim 5, wherein the illumination unit can be induced, using the measuring transducer, to operate at least one signal lamp in a flashing manner.

9. The measuring station of claim 8, wherein the measuring station has at least one command interface, by which command interface external commands can be received, wherein the measuring transmitter is configured to cause the illumination unit to operate at least one signal lamp in a flashing manner if a corresponding command is input.

10. The measuring station of claim 1, wherein the flow cell is of modular design, wherein modules of the flow cell are configured to accommodate at least one sensor.

11. The measuring station of claim 10, wherein at least one signal lamp is associated with each module.

12. The measuring station of claim 11, wherein the signal lamps have at least one illuminant including at least one of: a single color LED, an OLED, and a multicolor LED.

13. The measuring station of claim 12, wherein status signals from signal lamps correspond to the User Association of Automation Technology in Process Industries (NAMUR) standard NAMUR 107.

14. The measuring station of claim 1, wherein the flow cell includes a flow indicator, wherein the flow indicator includes an inductive proximity switch, and wherein at least one illumination unit is configured to indicate a respective state of the flow indicator.

15. The measuring station of claim 14, wherein the flow indicator is arranged in a module.

16. The measuring station of claim 14, wherein the flow indicator is configured to output a warning message given a low flow rate.

* * * * *